(12) United States Patent
Chiriva-Internati

(10) Patent No.: US 9,518,989 B2
(45) Date of Patent: *Dec. 13, 2016

(54) COMPOSITION AND METHOD FOR DIAGNOSIS AND IMMUNOTHERAPY OF LUNG CANCER

(71) Applicant: Texas Tech University System, Lubbock, TX (US)

(72) Inventor: Maurizio Chiriva-Internati, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/178,407

(22) Filed: Feb. 12, 2014

(65) Prior Publication Data

US 2015/0056252 A1 Feb. 26, 2015

Related U.S. Application Data

(60) Provisional application No. 61/763,629, filed on Feb. 12, 2013.

(51) Int. Cl.
| | |
|---|---|
| *A61K 39/00* | (2006.01) |
| *G01N 33/574* | (2006.01) |
| *C07K 16/30* | (2006.01) |
| *C07K 14/47* | (2006.01) |
| *C07K 14/705* | (2006.01) |
| *C12N 9/12* | (2006.01) |
| *A61K 35/15* | (2015.01) |

(52) U.S. Cl.
CPC ..... *G01N 33/57423* (2013.01); *A61K 39/0011* (2013.01); *C07K 14/47* (2013.01); *C07K 14/705* (2013.01); *C07K 16/3023* (2013.01); *C12N 9/12* (2013.01); *G01N 33/57488* (2013.01); *A61K 35/15* (2013.01); *A61K 2039/5154* (2013.01); *A61K 2039/572* (2013.01); *G01N 2333/47* (2013.01); *G01N 2333/705* (2013.01); *G01N 2333/912* (2013.01)

(58) Field of Classification Search
CPC .......................... A61K 39/0011; C12N 5/0639
USPC ............................... 424/277.1, 93.71, 93.21
See application file for complete search history.

(56) References Cited

U.S. PATENT DOCUMENTS

| | | | |
|---|---|---|---|
| 5,773,579 A | 6/1998 | Torczynski et al. | |
| 7,405,077 B2 * | 7/2008 | Lim et al. ............... | 435/372.3 |
| 2002/0168662 A1 * | 11/2002 | Lim et al. ............... | 435/6 |
| 2009/0017000 A1 | 1/2009 | Cai et al. | |
| 2010/0291156 A1 | 11/2010 | Barner et al. | |
| 2011/0287967 A1 | 11/2011 | Weinhausel et al. | |
| 2012/0100558 A1 | 4/2012 | Hanash et al. | |
| 2012/0263757 A1 | 10/2012 | Chiriva-Internati | |

FOREIGN PATENT DOCUMENTS

| | | |
|---|---|---|
| WO | 2009046974 A2 | 4/2009 |
| WO | 2011127418 A1 | 10/2011 |

OTHER PUBLICATIONS

Chiriva et al. (The Journal of Immunology, 2011, 186, Meeting Abstract No. 165.16).*
ISR PCT/US2014/016032 [KIPO] Dated May 28, 2014.
Nakagawa, K. et al., "XAGE-1 expression in non-small cell lung cancer and antibody response in patients", Clinical Cancer Research, 2005, vol. 11, pp. 5496-5503.
Figueiredo, D. L. A. et al., "High expression of cancer testis antigens MAGE-A, MAGE-C1/CT7, MAGE-C2/CT10, NY-ESO-1 and GAGE in advanced squamous cell carcinoma of the larynx", Head & Neck, 2011, vol. 33, pp. 702-707.
Errington, J.A. et al."Expression of cancer-testis antigens (MAGE-A1, MAGE-A3/6, MAGE-A4, MAGE-C1 and NY-ESO-1) in primary human uveal and conjunctival melanoma", British Journal of Ophathalmology, 2012, vol. 96, pp. 451-458.
Becker, S, et al. "Functional and clinical characterization of the putative tumor suppressor WWOX in non-small cell lung cancer," J Thorac Oncol. (Dec. 2011) 6:1976-83.
Bhan, S, et al. "BORIS binding to the promoters of cancer testis antigens, MAGEA2, MAGEA3, and MAGEA4, is associated with their transcriptional activation in lung cancer," Clin Cancer Res. (Jul. 1, 2011) 17:4267-76.
Bremnes, R M, et al. "The role of tumor infiltrating immune cells and chronic inflammation at the tumor site on cancer development, progression, and prognosis: emphasis on non-small cell lung cancer," J Thorac Oncol. (Apr. 2011) 6:824-33.
Caballero, O L et al. "Cancer/testis (CT) antigens: potential targets for immunotherapy," Cancer Sci. (Jul. 2009) 100:2014-21.
Chen, J, et al. "Atorvastatin synergizes with IFN-gamma in treating human non-small cell lung carcinomas via potent inhibition of RhoA activity," Eur J Pharmacol. (2012) 682:161-70.
Chinnasamy, N, et al. "A TCR targeting the HLA A* 0201-restricted epitope of MAGE-A3 recognizes multiple epitopes of the MAGE-A antigen superfamily in several types of cancer," J Immunol. (2011) 186:685-96.
Chiriva-Internati, M, et al. "AKAP-4: a novel cancer testis antigen for multiple myeloma: Br J Haematol," (Feb. 1, 2008) 40(4):465-8.
Chiriva-Internati, M, et al. "Cancer testis antigen vaccination affords long-term protection in a murine model of ovarian cancer," PLoS One. (May 2010) 5.

(Continued)

*Primary Examiner* — Yan Xiao
(74) *Attorney, Agent, or Firm* — Edwin S. Flores; Chainey P. Singleton; Chalker Flores, LLP

(57) ABSTRACT

The present invention includes compositions and methods for the diagnosis and treatment of lung cancer with a recombinant tumor-associated antigen loaded antigen presenting cell that generates a cytotoxic T lymphocyte specific immune response to at least one of SP17, AKAP-4, or PTTG1 expressed by one or more lung cancer cells.

8 Claims, 6 Drawing Sheets

(56) References Cited

OTHER PUBLICATIONS

Chiriva-Internati, M, et al. "Cancer testis antigen, ropporin, is a potential target for multiple myeloma immunotherapy," J Immunother. (2011) 34:490-9.

Chiriva-Internati, M, et al. "Identification of AKAP-4 as a new cancer/testis antigen for detection and immunotherapy of prostate cancer," Prostate. (2012) 72:12-23.

Chiriva-Internati, M, et al. "Sperm protein 17 (Sp17) is a suitable target for immunotherapy of multiple myeloma," Blood. (Aug. 1, 2002) 100:961-5.

Chiriva-Internati, M, et al. "Successful generation of sperm protein 17 (Sp17)-specific cytotoxic T lymphocytes from normal donors: implication for tumour-specific adoptive immunotherapy following allogeneic stem cell transplantation for Sp17-positive multiple myeloma," Scand J Immunol. (2002) 56:429-33.

Chiriva-Internati, M, et al. "Testing recombinant adeno-associated virus-gene loading of dendritic cells for generating potent cytotoxic T lymphocytes against a prototype self-antigen, multiple myeloma HM1.24," Blood. (Nov. 1, 2003) 102:3100-7.

Chiriva-Internati, M, et al. "The pituitary tumor transforming gene 1 (PTTG-1): an immunological target for multiple myeloma," J Transl Med. (Apr. 2008) 6:15.

Chiriva-Internati, M. "Sperm protein 17: clinical relevance of a cancer/testis antigen, from contraception to cancer immunotherapy, and beyond," Int Rev Immunol. (2011) 30:138-49.

Chrischilles, E A, et al. "Adverse events among the elderly receiving chemotherapy for advanced non-small-cell lung cancer," J Clin Oncol. (Feb. 1, 2010) 28:620-7.

Dadabayev, A R, et al. "Cancer immunotherapy targeting Sp17: when should the laboratory findings be translated to the clinics?" Am J Hematol. (Jan. 2005) 80:6-11.

Dubinett, S, et al. "Towards effective immunotherapy for lung cancer: simultaneous targeting of tumor-initiating cells and immune pathways in the tumor microenvironment," Immunotherapy. (Sep. 1, 2009) 5:721-5.

Gadgeel, S M "The optimal chemotherapy for stage III non-small cell lung cancer patients," Curr Oncol Rep. (Apr. 2011) 13:272-9.

Grizzi, F, et al. "Sperm protein 17 is expressed in human somatic ciliated epithelia," J Histochem Cytochem. (Apr. 1, 2004) 52:549-54.

Holt, G E, et al. "Immunotherapy as a strategy for the treatment of non-small-cell lung cancer," Therapy (Aug. 2011) 8:43-54.

Kim, S H, et al. "Expression of cancer-testis antigens MAGE-A3/6 and NY-ESO-1 in non-small-cell lung carcinomas and their relationship with immune cell infiltration," Lung. (Dec. 2009) 187:401-11.

Mathieu, M G, et al. "Cancer/testis antigens for therapeutic use," J Buon. 2009;14:S97-102. [abstract].

Mellman, I, et al. "Cancer immunotherapy comes of age," Nature. (Dec. 2011) 480:480-9.

Miller, P W, et al. "Intratumoral administration of adenoviral interleukin 7 gene-modified dendritic cells augments specific anti-tumor immunity and achieves tumor eradication," Hum Gene Ther. (Jan. 1, 2000) 11:53-65.

Mirandola, L, et al. "Cancer testis antigens: novel biomarkers and targetable proteins for ovarian cancer," Int Rev Immunol. (2011) 30:127-37.

O'Callaghan, D S, et al. "The role of inflammation in the pathogenesis of non-small cell lung cancer," J Thorac Oncol. (Dec. 2010) 5:2024-36.

Ortegel, J W, et al. "Modulation of tumor-infiltrating lymphocyte cytolytic activity against human non-small cell lung cancer," Lung Cancer. (2002) 36:17-25.

Paillard, C, et al. "NK cytotoxicity and alloreactivity against neuroblastoma cell lines in vitro: Comparison of Europium fluorometry assay and quantification by RT-PCR," J Immunol Methods. (Mar. 2012) 380:56-64.

Raez, L E, et al. "Lung cancer immunotherapy," Clin Med Res. (Sep. 2005) 3:221-8.

Rao, M, et al. "Inhibition of histone lysine methylation enhances cancer-testis antigen expression in lung cancer cells: implications for adoptive immunotherapy of cancer," Cancer Res. (Jun. 2011) 71:4192-204.

Santin, A D, et al. "Human papillomavirus type 16 and 18 E7-pulsed dendritic cell vaccination of stage IB or IIA cervical cancer patients: a phase I escalating-dose trial," J Virol. (Feb. 2008) 82:1968-79.

Santin, A D, et al. "Induction of human papillomavirus-specific CD4(+) and CD8(+) lymphocytes by E7-pulsed autologous dendritic cells in patients with human papillomavirus type 16- and 18-positive cervical cancer," J Virol. (Jul. 1999) 73:5402-10.

Sautes-Fridman, C, et al. "The immune microenvironments of lung and intraocular tumors," Bull Cancer. (Jun. 2011) 98:58-61.

Schneider, T, et al. "Non-small cell lung cancer induces an immunosuppressive phenotype of dendritic cells in tumor microenvironment by upregulating B7-H3," J Thorac Oncol. (Jul. 2011) 6:1162-8.

Shan, Q, et al. "A cancer/testis antigen microarray to screen autoantibody biomarkers of non-small cell lung cancer," Cancer letters. 2012.

Siegel R, Naishadham D, Jemal A. Cancer statistics, (2012) CA Cancer J Clin. 2012;62:10-29.

Song, J X, et al. "Anti-Sp17 monoclonal antibody with antibody-dependent cell-mediated cytotoxicity and complement-dependent cytotoxicity activities against human ovarian cancer cells," Med Oncol. (2011) 24:24.

Wang, J, et al. Strengths and weaknesses of immunotherapy for advanced non-small-cell lung cancer: a meta-analysis of 12 randomized controlled trials. PLoS One. (Mar. 2012) 7:5.

Xiang, R, et al. "A DNA vaccine targeting surviving combines apoptosis with suppression of angiogenesis in lung tumor eradication," Cancer Res. (Jan. 15, 2005) 65:553-61. 21.

Yasumoto, K, et al. "Lung cancer-associated tumor antigens and the present status of immunotherapy against non-small-cell lung cancer," Gen Thorac Cardiovasc Surg. (Sep. 2009) 57:449-457.

Shan Qiang et al: "A cancer/testis antigen microarray to screen autoantibody biomarkers of non-small cell lung cancer", Cancer Letters, vol. 328, No. 1, Jan. 2013 (Jan. 2013), pp. 160-167.

European Search Report (EP 14751009.3) Dated Feb. 8, 2016.

De Jong Ann et al: "Characterization of sperm protein 17 in human somatic and neoplastic tissue.", Cancer Letters, vol. 186. No. 2, Dec. 5, 2002 (Dec. 5, 2002), pp. 201-209.

Morten F Gjerstorff et al: "Analysis of GAGE, NY-ES0-1 and SP17 cancer/testis antigen expression in early stage non-small cell lung carcinoma", BMC Cancer, Biomed Central, London, GB, vol. 13. No. 1, 466, Oct. 8, 2013 (Oct. 8, 2013), pp. 1-6.

Gjerstorff M F et al; "Limited SP17 expression within tumors diminishes its therapeutic potential",Tissue Antigens, vol. 80, No. 6, Dec. 2012 (Dec. 2012), pp. 523-527.

Chiriva-Internati Maurizi0 et al: "Cancer Testis Antigens: A Novel Target in Lung Cancer",International Reviews of Immunology, vol. 31, No. 5, Oct. 2012 (Oct. 2012), pp. 321-343.

Extended Search Report [EP 14751009.3] dated May 16, 2016.

* cited by examiner

COMPOSITION AND METHOD FOR DIAGNOSIS AND IMMUNOTHERAPY OF LUNG CANCER

CROSS-REFERENCE TO RELATED APPLICATIONS

This application claims priority based on U.S. Provisional Application No. 61/763,629, filed Feb. 12, 2013. The contents of which is incorporated by reference in its entirety.

TECHNICAL FIELD OF THE INVENTION

One embodiment of the present invention relates in general to the field of detection of lung cancer and immunotherapy thereof, specifically to methods and compositions for diagnosis and treatment of lung cancer.

STATEMENT OF FEDERALLY FUNDED RESEARCH

None.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Feb. 24, 2014, is named TECH1081US_SeqList_022414.txt and is 2 kilobytes in size.

BACKGROUND OF THE INVENTION

Without limiting the scope of the invention, its background is described in connection with methods and compositions for diagnosis and treatment of lung cancer.

Lung cancer is the leading cause of cancer-related deaths, worldwide. Approximately 226,160 new cases and 160,340 deaths are expected in the Unites States in 2012 (1). The World Health Organization classifies lung cancer into four major histological types: (1) squamous cell carcinoma (SCC), (2) adenocarcinoma, (3) large cell carcinoma, and (4) small cell lung carcinoma (SCLC). The term non-small cell lung carcinoma (NSCLC) includes squamous, adenocarcinoma and large cell carcinomas.

Although the occurrence of breast cancer is slightly more common in the United States, lung cancer is second behind prostate cancer for males and third behind breast and colorectal cancers for women. Yet, lung cancer is the most common cause of cancer deaths. Typically, a combination of X-ray and sputum cytology is used to diagnose lung cancer. Unfortunately, by the time a patient seeks medical help for their symptoms, the cancer is at such an advanced state it is usually incurable.

The majority (85%) of lung cancer cases are of the non-small cell lung cancer (NSCLC) type and the 5-year survival rate for all patients diagnosed with NSCLC is estimated to be less than 20%. Standard treatments for NSCLC include chemotherapy, radiation therapy, surgery or a combination of these treatments. Unfortunately, these therapeutic interventions are associated with significant side effects (2), and generally offer patients limited benefits (3). Despite the recent addition of molecular target therapies to our armamentarium, the more recent addition to the armamentarium against NSCLC are targeted therapies. Unfortunately, despite the therapeutic advantages afforded by these agents such those based on the monoclonal antibodies bevacizumab, they can be used only in 16.5% of chemotherapy recipients (1, 4). NSLC is still is the leading cause of cancer-related deaths in the world. Therefore, there is an urgent need to develop more effective therapies for patients suffering from this devastating disease.

U.S. Pat. No. 5,773,579, entitled, "Lung cancer marker," discloses an isolated and purified nucleic acid sequence and corresponding amino acid sequence to a novel protein specific for human lung cancer cells. This gene is expressed at a much higher level in these cells than in normal lung cells, other normal tissues and other tumor cell lines tested. Also disclosed are three additional recombinant forms of this gene and protein, in the first two cases a membrane spanning region is removed and in the third case, an amino acid is changed by in vitro mutagenesis.

U.S. Patent Application Publication No. 2012/0100558, entitled, "Lung Cancer Diagnosis," is directed to the diagnosis of lung cancer in a subject before onset of symptoms in which the method includes screening a biological fluid from the subject for the presence therein of autoantibodies that are specific for one or more pre-diagnostic lung cancer indicator proteins, including LAMR1, and optionally additionally or alternatively including annexin I and/or 14-3-3-theta and/or other pre-diagnostic lung cancer indicator proteins as presently disclosed, as the defined antigens.

U.S. Patent Application Publication No. 2011/0177079, entitled, "Cancer-testis antigens," discloses cancer-testis antigens and the nucleic acid molecules that encode them. The invention also relates to the use of the nucleic acid molecules, polypeptides and fragments thereof in methods and compositions for the diagnosis and treatment of diseases, such as cancer. More specifically, the invention relates to the discovery of novel cancer-testis (CT) antigens.

U.S. Patent Application Publication No. 2010/0291156, entitled, "Composition for Treating Lung Cancer, Particularly of Non-Small Lung Cancers (NSCLC)," is directed to active (immunostimulatory) compositions with at least one RNA, preferably an mRNA, encoding at least two (preferably different) antigens capable of eliciting an (adaptive) immune response in a mammal. The invention is also said to teach a vaccine comprising said active (immunostimulatory) composition, and to the use of said active (immunostimulatory) composition (for the preparation of a vaccine) and/or of the vaccine for eliciting an (adaptive) immune response for the treatment of lung cancer, particularly of non-small cell lung cancers (NSCLC), preferably selected from the three main sub-types squamous cell lung carcinoma, adenocarcinoma and large cell lung carcinoma, or of disorders related thereto.

SUMMARY OF THE INVENTION

In one embodiment, the present invention includes a composition for the treatment of lung cancer comprising an isolated antigen presenting cell that has been loaded to present at least one SP17, AKAP-4, or PTTG1 tumor-associated antigens and that generates a cytotoxic T lymphocyte specific immune response to at least one of SP17, AKAP-4, or PTTG1, respectively, expressed by one or more lung cancer cells. In one aspect, the antigen presenting cell is a dendritic cell. In another aspect, the antigen presenting cell is an autologous dendritic cell. In another aspect, the composition further comprises at least one of NYESO-1, XAGE-1, ADAM29 and MAGEC1 antigens. In another aspect, the composition comprises a nucleotide sequence that codes for the recombinant SP17, AKAP-4, or PTTG1 tumor-associated antigen.

In another embodiment, the present invention includes a method for identifying a human subject suspected of having subject or at least at risk of developing lung cancer comprising the steps of: obtaining a sample from the subject; and determining the presence or absence of a specific immunoglobulin in the sample specific for at least one of anti-SP17, AKAP-4, or PTTG1, wherein the presence of the at least one of anti-SP17, AKAP-4, or PTTG1 specific immunoglobulin in the sample indicating the subject is afflicted with or at least at risk of developing lung cancer.

Another embodiment of the present invention includes a method for the determination of the tumor marker profile of an individual suffering from cancer comprising: obtaining a sample of bodily fluids from the individual; contacting the sample of bodily fluids from the individual with at least one of SP17, AKAP-4, or PTTG1 tumor-associated antigen; and determining the presence or absence of a complex of the at least one of SP17, AKAP-4, or PTTG1 tumor-associated antigen bound to one or more autoantibodies present in the sample of bodily fluids, wherein the one or more autoantibodies being immunologically specific to the at least one of SP17, AKAP-4, or PTTG1 tumor-associated antigen; wherein the presence of the complex provides the tumor marker profile of the individual, and wherein the tumor marker profile is determined as an indication of the course of disease. In one aspect, the presence of the complex indicates the detection of cancer. In another aspect, the cancer is lung cancer.

Yet another embodiment of the present invention includes an immunotherapeutic composition for the treatment of cancer comprising at least one of an SP17, AKAP-4, or PTTG1 tumor-associated antigen capable of generating an SP17, AKAP-4, or PTTG1 specific cytotoxic T lymphocyte specific for one or more lung cancer cells. In one aspect, the composition further comprises at least one antigen presenting cell. In one aspect, the antigen presenting cell is a dendritic cell. In another aspect, the at least one antigen presenting cell is a pulsed or loaded with the peptide or an expression construct encoding the SP17, AKAP-4, or PTTG1 tumor-associated antigen. In another aspect, the at least one of an SP17, AKAP-4, or PTTG1 tumor-associated antigen is isolated from a non-small cell lung carcinoma.

Another embodiment of the present invention includes a method for detecting lung cancer in a subject comprising the steps of: obtaining a sample from the subject; and determining the presence or absence of SP17, AKAP-4, or PTTG1 in the sample, wherein the presence of SP17, AKAP-4, or PTTG1 in the sample indicates the subject is afflicted with or at least at risk for developing lung cancer. In one aspect, the sample is a blood sample.

Another embodiment of the present invention includes a composition comprising a nucleic acid vector that expressed an immunostimulatory antigen, wherein the antigen comprises the nucleotide sequence coding for at least one of an SP17, AKAP-4, or PTTG1 lung cancer-associated antigen. In another aspect, the antigen is a peptide antigen.

Yet another embodiment of the present invention includes a method for the treatment of cancer comprising the steps of: administering to a mammal in need thereof a synergistic, therapeutically effective amount of a lung cancer antigen, in addition to at least one of diluents, vehicles, excipients, or inactive ingredients; generating a specific cytotoxic T lymphocytes (CTL) from the lung cancer antigen; and targeting one or more tumor cells with the specific cytotoxic T lymphocytes. In one aspect, the lung cancer antigen is SP17, AKAP-4, or PTTG1.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
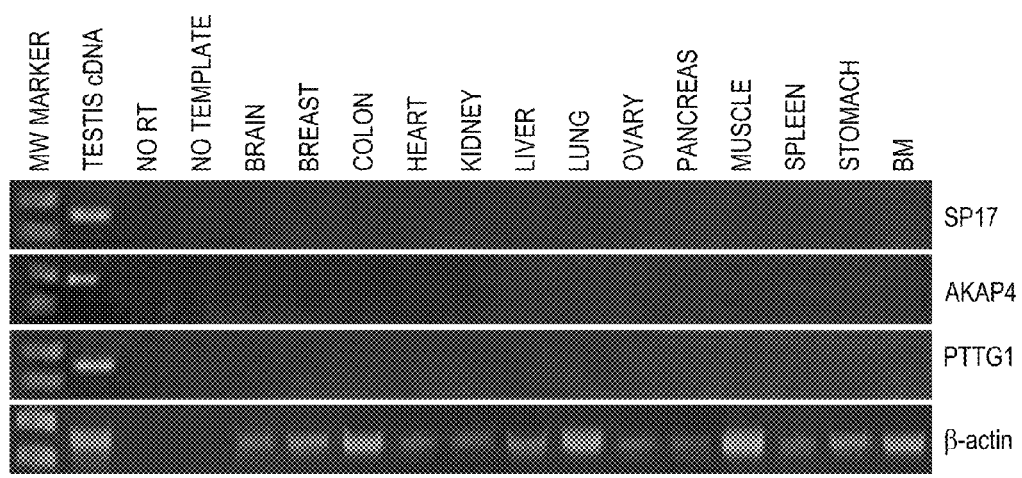
FIGS. 1A-1C are images showing RT-PCR analysis of Cancer/testis antigens (CTA) expression.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "antigen" and the term "epitope" refers to a molecule or substance capable of stimulating an immune response. In one example, epitopes include but are not limited to a polypeptide and a nucleic acid encoding a polypeptide, wherein expression of the nucleic acid into a polypeptide is capable of stimulating an immune response when the polypeptide is processed and presented on a Major Histocompatibility Complex (MHC) molecule. Generally, epitopes include peptides presented on the surface of cells non-covalently bound to the binding groove of Class I or Class II MHC, such that they can interact with T cell receptors and the respective T cell accessory molecules. However, antigens and epitopes also apply when discussing the antigen binding portion of an antibody, wherein the antibody binds to a specific structure of the antigen.

Proteolytic Processing of Antigens. Epitopes that are displayed by MHC on antigen presenting cells are cleavage peptides or products of larger peptide or protein antigen precursors. For MHC I epitopes, protein antigens are often digested by proteasomes resident in the cell. Intracellular proteasomal digestion produces peptide fragments of about 3 to 23 amino acids in length that are then loaded onto the MHC protein. Additional proteolytic activities within the cell, or in the extracellular milieu, can trim and process these fragments further. Processing of MHC Class II epitopes generally occurs via intracellular proteases from the lysosomal/endosomal compartment. The present invention includes, in one embodiment, pre-processed peptides that are attached to the anti-CD40 antibody (or fragment thereof) that directs the peptides against which an enhanced immune response is sought directly to antigen presenting cells.

To identify epitopes potentially effective as immunogenic compounds, predictions of MHC binding alone are useful but often insufficient. The present invention includes methods for specifically identifying the epitopes within antigens most likely to lead to the immune response sought for the specific sources of antigen presenting cells and responder T cells.

The present invention allows for a rapid and easy assay for the identification of those epitopes that are most likely to produce the desired immune response using the patient's own antigen presenting cells and T cell repertoire. The compositions and methods of the present invention are applicable to any protein sequence, allowing the user to identify the epitopes that are capable of binding to MHC and are properly presented to T cells that will respond to the antigen. Accordingly, the invention is not limited to any particular target or medical condition, but instead encompasses and MHC epitope(s) from any useful source.

Over the past years, immunotherapy has emerged as a promising therapy for several types of cancer including melanomas, renal cell carcinomas and, more recently, lung cancer (5). The generation of antitumor immune responses directed against specific tumor-associated antigens has the potentially of promoting neoplastic cell death with few deleterious effects on normal tissues and minimal toxicities (5). Cancer/testis antigens (CTAs) are a family of proteins with testis-restricted expression and negligible expression in normal tissues. Interestingly, CTAs are frequently expressed in many tumors at the mRNA and protein levels (6-10). More recently, the CTAs NY-ESO-1 and MAGE-A2/3/4/6, have been detected in Non-Small Cell Lung Cancer (NSCLC) primary tumors and their immunogenicity suggests indicates they are promising targets for potentially effective lung cancer vaccines (11-14). The inventors have previously validated the CTAs SP17, AKAP4, Ropporin, and PTTG1 as potential immunotherapeutic targets in ovarian cancer, multiple myeloma, and prostate cancer (6, 15-17). In the effort to identify novel antigens that could be exploited as potential targets for lung cancer immunotherapies, the inventors demonstrate herein the RNA and protein expression pattern of SP17, AKAP4 and PTTG1 in NSCLC cell lines and primary tumor samples from NSCLC patients as well as their immunogenicity by measuring the presence of CTA specific antibodies (Abs) in sera of lung cancer patients and the feasibility of generating CTA-specific cytotoxic anti-tumor responses in vitro, using autologous peripheral blood mononucleated cells (PBMCs).

Although NSCLC was historically thought to be weakly immunogenic because of the low frequency of tumor-infiltrating T cells (21), studies using murine NSCLC models have shown that is it possible to activate an effective immune response utilizing a DC-based approach (22, 23). In addition, tumor antigen-specific T cell responses have been detected in patients with NSCLC (23), indicating that identifying specific NSCLC-associated antigens and presenting them in an optimal fashion to the immune system may generate tumor-specific effector T cells generally absent or inactive in this disease (24). The potential role of immunotherapy in improving patients' survival and reducing morbidities associated to standard treatments has been demonstrated by a recent meta-analysis of clinical vaccine trials in patients with NSCLC (25). When studying an immunotherapy-based anticancer strategy, the choice of antigens to be targeted by the vaccine is a critical step (5). Ideal targets should be highly immunogenic proteins selectively expressed in cancer cells but not in normal cells (5, 10). CTAs are tumor-associated antigens particularly suitable for tumor immunotherapy due to their highly tumor-restricted expression pattern and their immunogenicity (7, 9).

The present invention provides the use of three CTA, namely SP17, AKAP4, and PTTG1, in the immunotherapy of NSCLC. The inventors analyzed for the first time the differential expression of 3 CTAs, namely SP17, AKAP4, and PTTG1, in a panel of normal tissues, three NSCLC cell lines, one normal bronchus cell line, primary tumor cells from 17 NSCLC patients, and bronchus epithelial cells from 8 healthy subjects. None of the nontumoral tissues expressed RNA levels for the selected CTAs, with the exception of the testis (7, 10). NSCLC cell lines expressed SP17, AKAP4, and PTTG1 transcripts and proteins, while the normal bronchus epithelium cell line showed weakly SP17 RNA expression only. This is consistent with the inventors' previous report showing that SP17 is expressed in ciliated somatic epithelia, including those of the airways (26). Interestingly, independent preclinical studies strongly suggest that 14 SP17-directed immunotherapies do not result in any toxicity related to SP17-expression in ciliated cells (16, 27, 28). All of the lung cancer tissues derived from patients demonstrated SP17 expression at the transcriptional and translational levels, while the majority of specimens also displayed AKAP4 and PTTG1 expression. Results for protein expression were confirmed independently by flow-cytometry and immunofluorescence, with consistent results. Tumors from 16 out of 17 NSCLC subjects showed expression of at least two out of three CTAs studied, suggesting their potential importance in this disease. For a protein to serve as a target for immunotherapy it should be able to elicit a strong and measurable immune response, a characteristic known as immunogenicity. The present inventors found that the majority of NSCLC patients' sera were positive for at least two CTA-specific antibodies, with only patient #5 displaying anti-SP17 but not anti-AKAP4 or anti-PTTG1 IgG. While there was a complete concordance between mRNA and protein expression data in tumor tissues, the humoral antitumor response, measured as anti-CTA antibodies in sera, resulted more heterogeneous. For example, three NSCLC patients (#2, 13, 14) were classified as anti-SP17 negative, although their tumors expressed SP17. Interestingly, all of the AKAP4- or PTTG1-positive patients also displayed the corresponding specific autoantibodies in their sera. A recent study by Shan Q. et al. (29). generated a low-density protein microarray containing 72 CTAs and probed it with the serum from NSCLC patients and healthy subjects. These investigators reported the detection of NYESO-1, XAGE-1, ADAM29 and MAGEC1 Abs, in the serum of NSCLC patients. These finding indicates anti-CTA antibodies could be exploited as a diagnostic tool in NSCLC.

To determine if SP17, AKAP4, and PTTG1 immunogenicity could generate a CTA/tumor-specific CTL response, the inventors examined T cell response to CTA-loaded dendritic cells (DCs). The application of DCs is a widely recognized method for the stimulation of tumor antigen-specific T cell responses and the present inventors have previously used this technique in MM, cervical and prostate cancer (6, 15, 30, 31). To study the feasibility of generating CTA-specific CTLs from PBMCs, the present inventors selected 5 patients that tested positive for SP17, AKAP4, or PTTG1 protein expression in tumor cells. Patients' PBMCs stimulated with CTA-presenting DCs displayed significant lytic activity against autologous lung cancer cells and NSCLC-derived cell lines. The observed cytotoxic effect was restricted for HLA class I positive targets, as it was blocked by anti-HLA class I but not by anti-HLA class II antibodies. Antigenic specificity for CTL lytic activity was confirmed by their inability to generate a cytotoxic response against the CTA-negative CRL-2503 cells or following exposure to either non-pulsed DCs or DCs loaded with HPV E7 antigen. Cytokine expression analysis revealed that the inventors' DC-based CTL generation protocol induced a strong Th-1 polarization in stimulated PBMCs, as confirmed by increased IFN-γ and TNF-α and decreased IL-4, IL-5, and IL-10 levels (6, 16, 19, 31-33). Since NSCLC patients show an abnormal Th-2-type cytokine pattern (34), which negatively impacts a significant response to immunotherapy (35), it is possible (but not a limitation of the present invention) that the ability of CTA-loaded DCs to stimulate a T-helper Th-1 profile is clinically relevant (36). The activation of effector T lymphocytes was further demonstrated by ELISPOT analysis, which revealed a high frequency of IFN-γ-expressing cells in PBMCs primed with CTA-loaded DCs and exposed to autologous tumor cells. This is finding is relevant, since IFN-γ has been shown to exert significant inhibitory effects in NSCLC growth (37). The feasibility of generating an active CTA-specific immune response in vitro indicates that expression of CTAs by NSCLC cells could have therapeutic relevance and serve as the basis for designing novel immunotherapeutic strategies against this disease. Moreover, DCs engineered in vitro to effectively present CTAs to effector T cells may overcome the immunosuppression seeing in NSCLC's tumor microenvironment allowing the development of effective vaccination strategies against this disease (38-40).

The present invention provides that the CTAs: SP17, AKAP-4, and PTTG1, are selectively expressed in NSCLC and that their expression can be exploited to generate specific CTL-mediated antitumor responses. The expression and immunogenicity of SP17, AKAP4, and PTTG1 in multiple myeloma, ovarian and prostate cancer (6, 16, 17, 19, 31, 32), and now in NSCLC, indicates the use of targeting these CTA expressing tumors with a CTA-driven vaccination strategy.

The NSCLC cell lines CRL-5928 (squamous cell carcinoma), CRL-5922 (adenocarcinoma), and the immortalized, non-tumorigenic human bronchial epithelial cell line CRL-2503 (established by transfection with the origin of replication-defective SV40 large T plasmid), were from the American Type Culture Collection (Manassas, Va., USA) and were maintained in RPMI-1640 medium (Invitrogen, Carlsbad, Calif., USA) supplemented with 10% V/V FBS (Invitrogen, Carlsbad, Calif., USA) at 37° C. and 5% $CO_2$.

The present inventors evaluated 17 NSCLC tumor samples derived from surgical procedures and 8 samples from healthy subjects who underwent bronchial biopsy. Sera were collected at the time of routine blood tests as previously described (6). Materials from human subjects were obtained with approval from the local ethics committee and the patients' informed consent. Punch biopsies were minced and tissue fragments were plated in complete medium (RPMI-1640 medium supplemented with 10% FBS, 20 mM HEPES buffer, 100 U/mL penicillin, 100 mg/mL streptomycin). Cells were maintained in 5% $CO_2$ and 37° C. for 24 hours prior to analysis. The normal tissue panel was from Applied Biosystems (Foster City, Calif.). SP17: 5'Sp17 PCR SEQ ID NO: 1-5'-GGC AGT TCT TAC CAA GAA GAT-3'; for 3'Sp17 PCR SEQ ID NO:2-5'-GGA GGT AAA ACC AGT GTC CTC-3'; AKAP4: SEQ ID NO:3-5'-GCG TAC TCT GAT ACT ACA ATG ATG-3' and SEQ ID NO:4-5'-GGG 6 GTT TTG GGT AAA GTC A-3'; PTTG1: SEQ ID NO:5-5'-GGT TTA AAC CAG GAG TGC CGC-3' and SEQ ID NO:6-5'-AAT TCA ACA TCC AGG GTC GAC AG-3'; β-actin: SEQ ID NO:7-5'-CGT CTT CCC CTC CAT CG-3' and SEQ ID NO:8-5'-CTC GTT AAT GTC ACG CAC-3' (35 cycles, 55° C. annealing temperature). PCR products were visualized on an ethidium bromide agarose gel for a DNA band of the expected size. All results were confirmed in three independent RT-PCRs experiments.

Approximately 400,000 cells were washed with PBS 1× and fixed with buffered paraformaldehyde (4% W/V in PBS 1×, pH=7.4). Cells were then permeabilized for 5 minutes on ice with permeabilization buffer (0.3% V/V saponin in PBS), and incubated with specific primary Abs: goat anti-human SP17, goat anti-human AKAP4 (both from Santa Cruz Biotechnology, Inc. Santa Cruz, Calif., USA), or rabbit anti-human PTTG1 (Novus Biologicals, LLC, Littleton, Colo., USA). Negative controls were obtained with cells incubated with equal amounts of matching isotypic Abs (Novus Biologicals, LLC, Littleton, Colo., USA). After 1 hour incubation on ice, cells were washed three times in permeabilization buffer, then incubated 20 minutes on ice with the appropriate FITC-conjugated secondary antibody (BD Biosciences, San Jose, Calif., USA). Fluorescence intensity was measured using a FACS-Canto flow cytometer (BD).

Immunofluorescence evaluation of CTA expression was performed as previously described (15). 20,000 cells were subjected to cytospin and fixed with SlideRite (Fisher), and air-dried overnight. Each sample was permeabilized in a 0.1% Triton X-100 sodium citrate buffer for 15 minutes at 4° C. cells were then incubated overnight in a wet chamber at 4° C. with the specific primary antibodies described in the flow-cytometry methods (1:100 dilution in PBS/BSA 0.1%) and then with phycoerythrin-conjugated rabbit IgG secondary antibodies (1:500 dilution, 7 Abcam). Results were analyzed by inverted fluorescence microscope (Olympus IX71 inverted microscope equipped with laser), and pictures were taken at 60× objective magnifications. Standard DAPI staining was used to detect the nuclei.

Polystyrene 96-well plates were coated with human recombinant proteins (SP17, AKAP4 or PTTG1, all from Novus Biologicals, LLC, Littleton, Colo., USA) in 50 μL carbonate coating buffer (10 μg/well) for 2 hours at 23° C. under gentle agitation. After washing twice with 100 μL PBS, unspecific binding sites were blocked with 1% W/V BSA in PBS for 1 hour at 23° C. Then, BSA was removed and 50 μL sera were added (diluted 1:5 in PBS). After 1 hour incubation at 34° C., plates were washed twice with 100 μL washing buffer (0.05% V/V Tween-20 in PBS), and incubated with HRP-linked mouse anti-human IgG (Abcam, diluted 1:4,000 in PBS). After 1 hour incubation at 22° C. in the dark, plates were washed twice with 100 μL washing buffer, then incubated with HRP substrate solution (Kpl ABSTO Peroxidase Substrate System) in the dark for 5 minutes at 22° C. Absorbance was read at 405 nm (0.1 s/well). Absorbance of negative controls (antigen-free wells incubated with commercial antibodies) was subtracted to that obtained in well incubated with sera.

Heparinized blood was centrifuged in a Ficoll-Hypaque density gradient to separate PBMCs from 5 patients. PBMCs were seeded into 6-well culture plates with 3 mL RPMI-1640 medium and 10% FBS at 8-10×106 cells/well. After 2 hours at 37° C. and 5% CO2, the present inventors removed the nonadherent cells and cultured the adherent cells in RPMI-1640 supplemented with 10% FBS, 1000 IU/mL interleukin 4 (IL-4) and 800 IU/mL granulocytes-macrophage colony-stimulating factor 8 (GM-CSF). After 1 week of culture, DCs were harvested and pulsed with human recombinant SP17, AKAP4 or PTTG1 as described (6, 15).

DCs were washed twice and placed in a 50 mL polypropylene tube. Recombinant proteins were mixed with the cationic lipid DOTAP (Roche, Mannheim, Germany) at room temperature for 20 minutes, and added to the DCs for 3 hours at 37° C., with occasional agitation.

Antigen-pulsed DCs were co-cultured with fresh autologous PBMCs (6) at a ratio of 1:10 in RPMI-1640 with 10% autologous serum, 10 IU/mL IL-2 and 5 ng/mL IL-7 at 37° C., 5% $CO_2$. Irradiated autologous PBMCs feeder cells and recombinant CTAs (50 μg/mL) were added once a week, and IL-2 was added every 3 days. Recombinant CTA were endotoxin-free, as confirmed by endotoxin detection assay performed through the ToxinSensor Chromogenic LAL Endotoxin Assay Kit (GenScript USA Inc., 08854, NJ).

To test the cytotoxic activity of the CTA-stimulated T cells, the present inventors performed a EUROPIUM-based cytotoxicity assay using the DELFIA® EuTDA system according to the manufacturer's directions (Perkin Elmer, USA). Target cells included autologous DCs (unstimulated or pulsed with the lung-cancer irrelevant HPV-E/antigen), and autologous tumor cells (at the effector-target cell ratios of 40:1, 20:1, or 10:1). Antibodies against HLA class I (W6/32) and HLA class II (L243) were added at a concentration of 25 μg/mL to evaluate HLA restricted cytotoxicity, with a fixed 20:1 effector:target ratio.

ELISA was performed on the supernatants of activated PBMCs and autologous tumor cells 4 hours co-culture (20:1 effector:target ratio). The U-CyTech sandwich ELISA kits (U-CyTech, Utrecht, The Netherlands) was used for the detection of human IL-4, IL-5, IL-10, interferon (IFN)-γ, and tumor necrosis factor α (TNF)-α, in accordance with the manufacturer's directions. Reactions were developed by adding TMB Microwell substrate, stopping the reaction by the addition of 2M $H_2SO_4$. The absorbance was read at 450 nm. Data are presented as the ODs measured with activated PBMCs divided by the ODs obtained with PBMCs incubated with autologous DCs without antigens (OD ratio).

IFN-γ expression by patients' CTLs (20:1 effector:target ratio) was evaluated using ELISPOT assay (UCyTech, Utrecht, The Netherlands), according to the manufacturer's directions as the present inventors described elsewhere (15). Spots counts were performed with an AID ELISPOT Reader System (Cell Technology, Inc., Columbia, Md.).

Figure 1B:
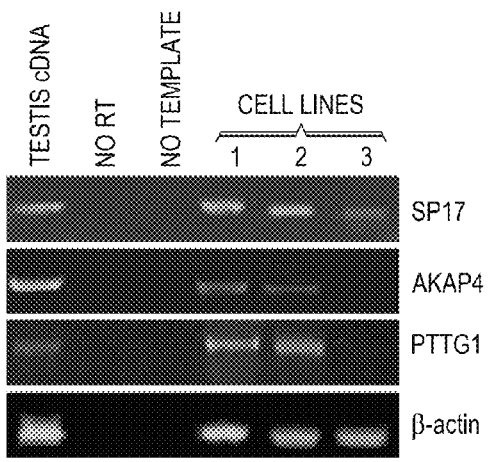
Figure 1C:
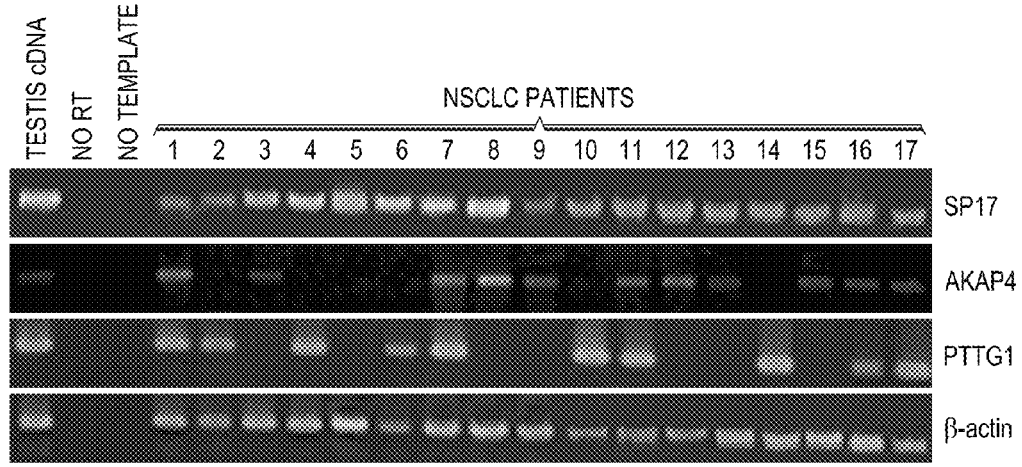

FIGS. 1A-1C are images showing RT-PCR analysis of CTA expression. FIG. 1A is an image of a gel showing PCR on cDNA prepared from a normal tissue panel. FIG. 1B is an image of a gel showing PCR on cDNA from NSCLC cell lines CRL-5928 (1), CRL-5922 (2), or the normal bronchus epithelium-derived cells CRL-2503 (3). FIG. 1C is an image of a gel showing PCR on cDNA from NSCLC primary tumors. Positive control was cDNA prepared from the testis, while negative controls were PCR performed with RNA without previous retro-transcription (no RT), and PCR performed without template (no template). β-actin was used to confirm successful retro-transcription. It was found that SP17/AKAP4/PTTG1 RNA is selectively expressed by NSCLC cell lines and primary tumors, but not in nontumoral cell lines and tissues. Gene expression of SP17, AKAP4, and PTTG1, was determined with RT-PCR using RNA from a panel of normal tissues as seen in FIG. 1A. Three cell lines (two derived NSCLC and one derived from normal bronchus epithelium are shown in FIG. 1B, and a cohort of 17 patients newly diagnosed with NSCLC is shown in FIG. 1C. As a positive control, the present inventors analyzed CTA expression in the testis (6, 16, 17), while negative controls were obtained using pooled RNA that did not undergo retro-transcription (to exclude possible amplification of contaminating genomic DNA) and in which RT-PCR was performed without template. While none of the normal tissues expressed detectable RNA levels for SP17, AKAP-4 and PTTG1, (as seen in FIG. 1A), the normal bronchial cell line CRL-2503 demonstrated weak expression of SP17 RNA (as seen in FIG. 1B). The NSCLC cell lines CRL-5928 and CRL-5922 demonstrated significant RNA expression of the three CTAs evaluated (as seen in FIG. 1B). Moreover, tumors from all 17 NSCLC patients were positive for SP17 while 65% of tumors expressed AKAP4 (11/17), and 59% PTTG1 (10/17) (as seen in FIG. 1C).

Figure 2:
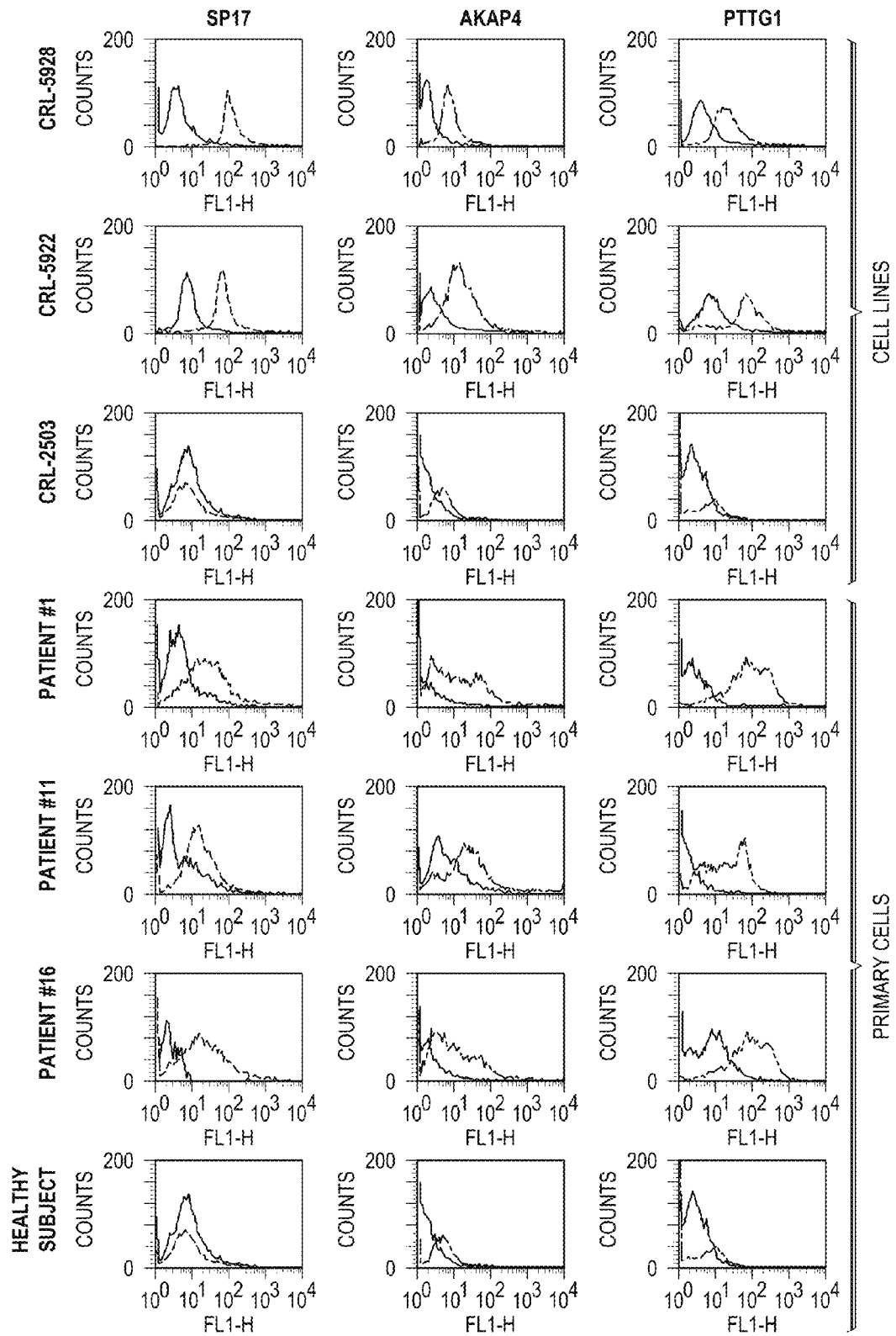
FIG. 2 shows flow-cytometry analysis of cells incubated with the indicated antibody and corresponding isotypic controls.

FIG. 2 shows flow-cytometry analysis of cells incubated with the indicated antibody (colored histograms) or corresponding isotypic controls (black histograms). Fluorescence intensity was measured on FSC/SSC-gated cells (10,000 events) in the FL1 channel (Log scale) using a FACS-Canto flow cytometer (BD). The plots are arranged by SP17 AKAP4 and PTTG1 in cell lines and primary patients' samples. SP17, AKAP4 and PTTG1 are expressed at the protein level by NSCLC cell lines and primary patients' samples, but not by normal bronchus epithelium. To study the expression of the CTA panel at the protein level, the present inventors performed a flow-cytometry analysis by CTA-specific antibody staining of permeabilized cells. FIG. 2 shows that SP17, AKAP4 and PTTG1 are expressed by NSCLC-derived but not by normal bronchus-derived cell lines. Of note, nontumoral CRL-2503 cells were negative for SP17 protein, even though the SP17 gene was weakly expressed (FIGS. 1B and 2). The present inventors performed a similar analysis on patient-derived NSCLC tumors/tissues, which was fully consistent the RT-PCR data. FIG. 2 shows representative results from 3 patients. The specificity of CTA expression was confirmed 11 by the absence of SP17, AKAP4, and PTTG1 positive staining in tissues derived from one of the healthy individuals evaluated (e.g., a representative result is displayed in FIG. 2). To further assess the expression of selected CTA in tumoral and normal cells, the present inventors performed immunofluorescence analysis of cytospun NSCLC cell lines, a normal bronchus cell line, and cells derived from primary tumors.

Figure 3:
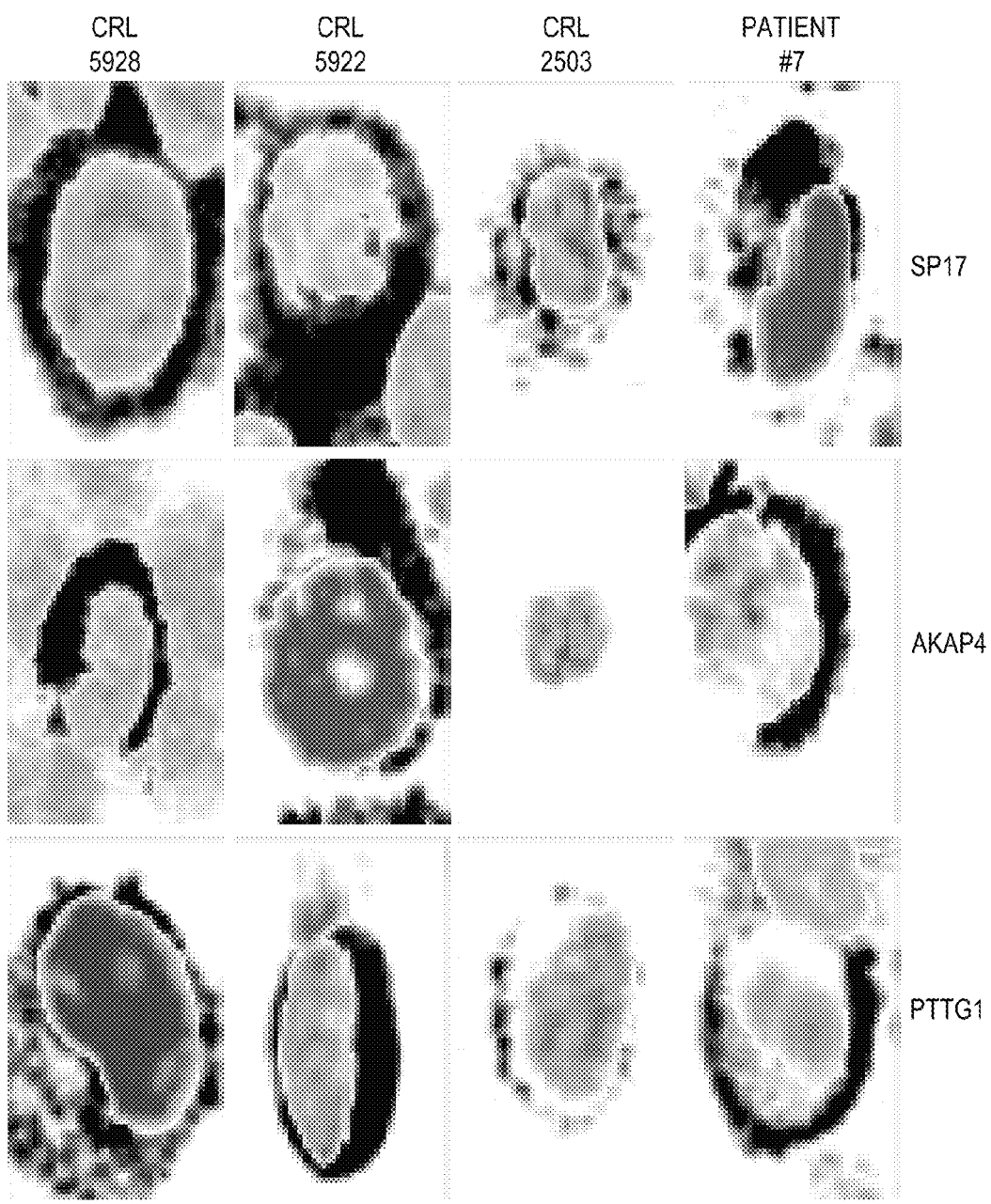
FIG. 3 shows immunofluorescence performed on NSCLC cell lines, CRL-5928, CRL-5922, on the normal bronchus epithelium-derived cells CRL-2503, and one representative patient.

FIG. 3 shows immunofluorescence performed on NSCLC cell lines, CRL-5928, CRL-5922, on the normal bronchus epithelium-derived cells CRL-2503, and one representative patient. Representative immunofluorescence performed on NSCLC cell lines, CRL-5928, CRL-5922, on the normal bronchus epithelium-derived cells CRL-2503, and one representative patient (#7). The present inventors show the positive stain for SP17, AKAP4, and PTTG1 (green signal) in the cytoplasm. Pictures were taken at 60× magnification by an inverted florescence microscope (Olympus IX71). To measure a possible humoral response against SP17, AKAP4, and PTTG1, the present inventors compared the levels of circulating CTA-specific IgG autoantibodies in sera from NSCLC patients with those from healthy subjects, by indirect ELISA. A subject was considered positive if the ELISA signal was at least 3 standard deviations higher than the median signal found in healthy subjects (20).

Figure 4A:
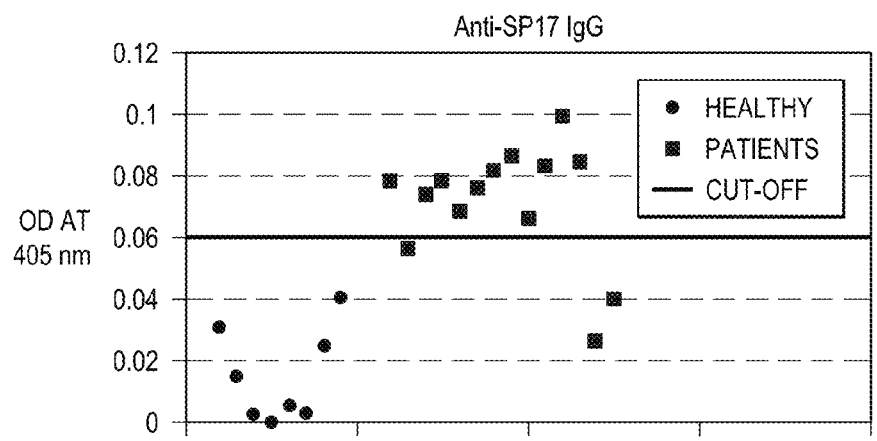
FIGS. 4A-4C are graphs of enzyme linked immunosorbent assay (ELISA) data for the detection of circulating CTA-specific IgG.
Figure 4B:
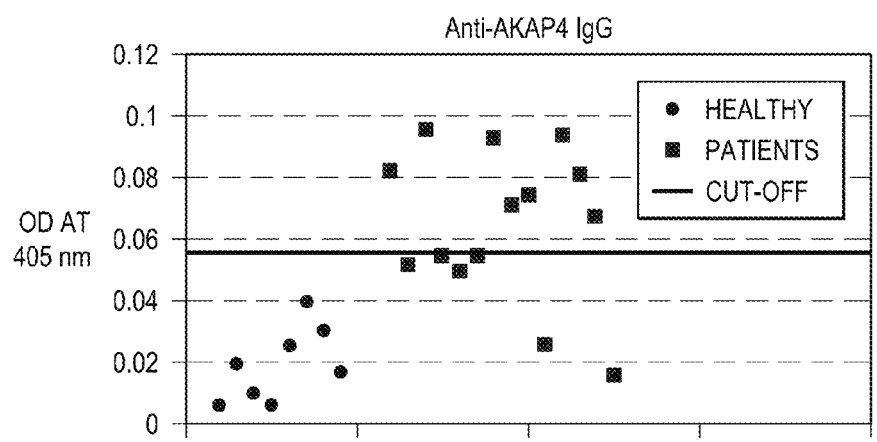
Figure 4C:
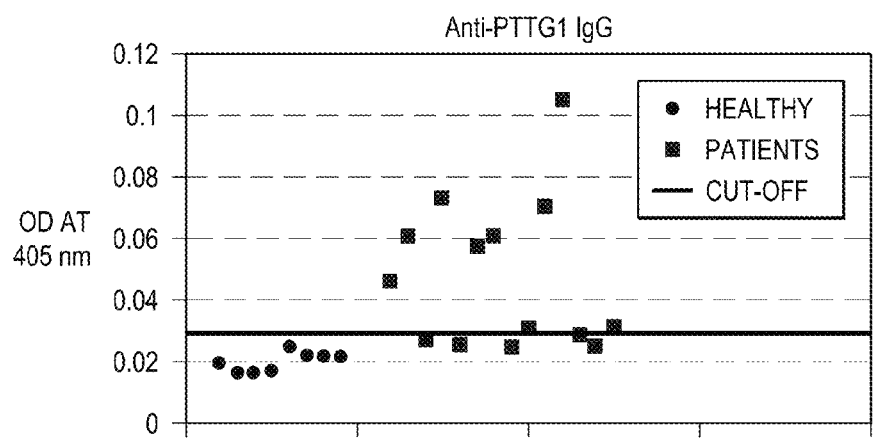
Figure 5A:
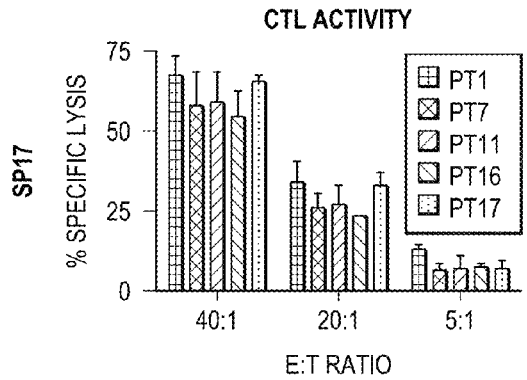
FIGS. 5A-5F are graphs of the analysis of Cytotoxic T-Lymphocyte (CTL) activity and specificity.
Figure 5B:
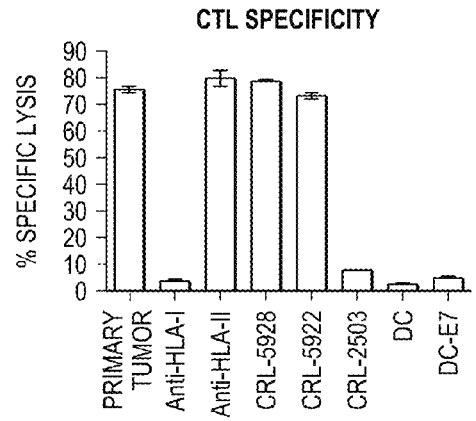
Figure 5C:
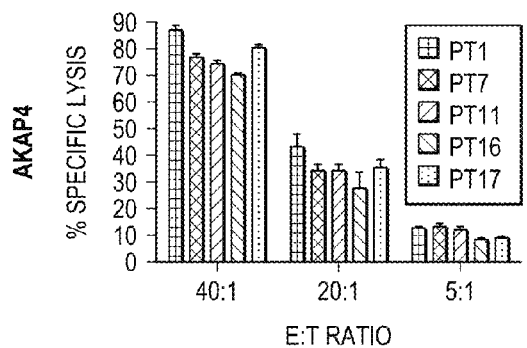
Figure 5D:
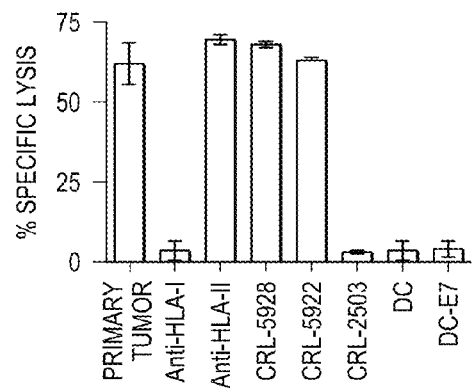
Figure 5E:
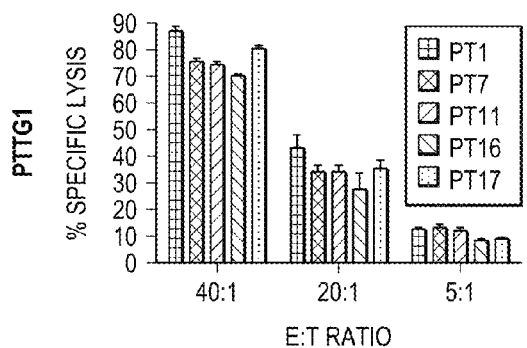
Figure 5F:
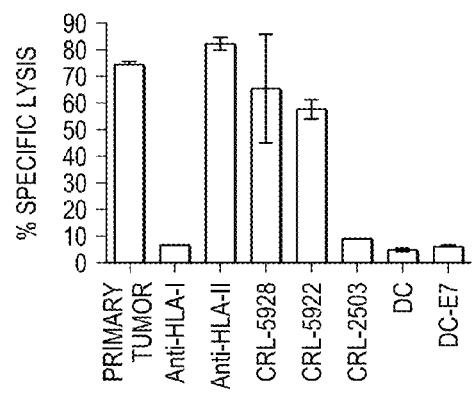

FIGS. 4A-4C are graphs of ELISA data for the detection of circulating CTA-specific IgG for SP17, AKAP4, and PTTG1. FIGS. 4A-4C ELISA for the detection of circulating CTA-specific IgG. Graphs display mean OD values calculated from studies run in triplicate (squares, NSCLC patients' sera; diamonds, healthy subjects' sera). The horizontal line represents the positivity cut-off, calculated as three times the median value obtained from the healthy control group. Consistently with expression data from RT-PCR, flow-cytometry and immunofluorescence, FIGS. 4A-4C show that the majority of NSCLC patients displayed CTA specific circulating autoantibodies.

FIGS. 5A-5F are graphs of the analysis of CTL activity and specificity. The histograms show the percentage of specific lysis obtained through a non-radioactive EURO-PIUM-based assay under the indicated different conditions. The left panel shows the CTL activity at different ratios of effector (E): target 22 (T) cells. Bars represent the mean of experiments run in triplicate, and error bars represent standard deviations. The right panel shows the analysis of CTL specificity. Bars represent the mean values obtained from experiments run on the selected 5 patients, while error bars represent standard deviations. Antibodies against HLA class I (W6/32) and HLA class II (L243) were added, at a concentration of 25 µg/mL to evaluate HLA restricted cytotoxicity. CTL indicates cytotoxic T lymphocyte; DC, dendritic cell; HLA, human leukocyte antigen; E7, HPVE7 antigen; PBMCs, peripheral blood mononucleated cell. The present inventors successfully generated CTLs capable of efficiently killing autologous tumor cells from 5 patients as seen in FIGS. 5A-F left column. For this analysis, the present inventors selected the patients that displayed specific CTA expression at the protein level in their tumor cells. The specificity of cytotoxic effect was supported by the high percentage of lysis of autologous tumor cells and NSCLC-derived cell lines (40% to more than 80%), whereas non-tumoral cells (DC, DC pulsed with the unrelated HPV-E7 antigen, and the normal bronchus-derived cell line CRL-2503) were lysed in <10% (FIGS. 5A-F, right). HLA class I restriction was shown by lysis inhibition by an antibody directed 12 against monomorphic HLA class I molecules, but not HLA class II molecules as seen in FIGS. 5A-F, right column.

Figure 6A:
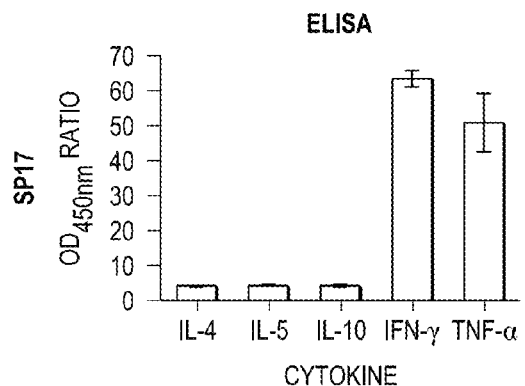
FIGS. 6A-6F are ELISA analyzed for the levels of the indicated cytokines and ELISPOT analysis of IFN-γ expression by patients' CTLs co-cultured with autologous tumor cells.
Figure 6B:
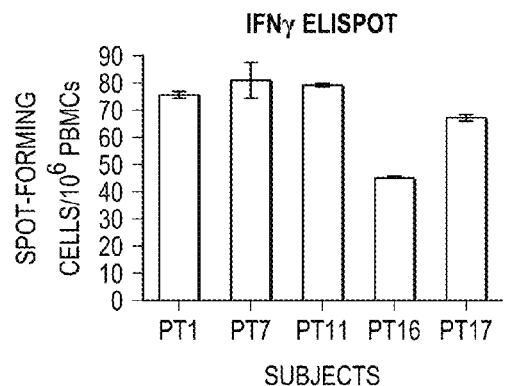
Figure 6C:
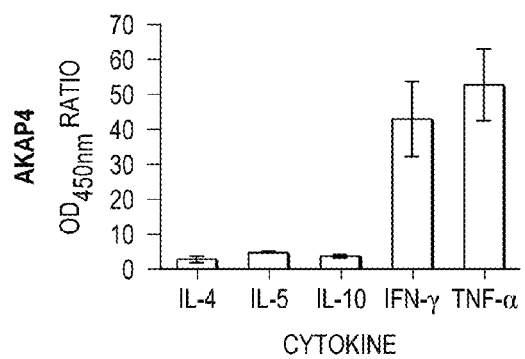
Figure 6D:
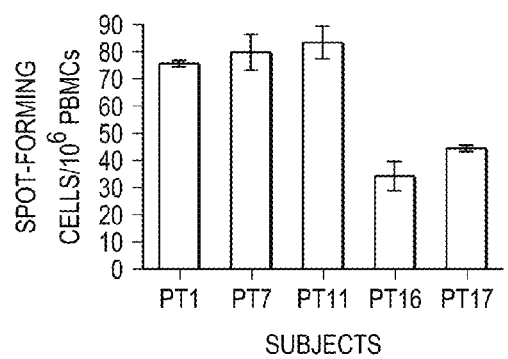
Figure 6E:
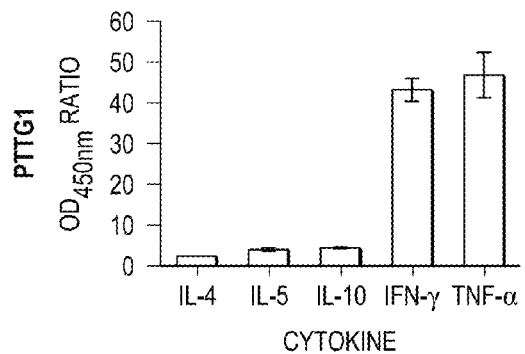
Figure 6F:
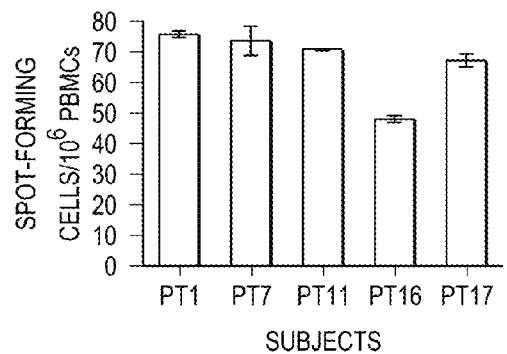

FIGS. 6A, 6C and 6E are ELISA analyzed for the levels of the indicated cytokines and FIGS. 6B, 6D and 6F are ELISPOT analysis of IFN-γ expression by patients' CTLs co-cultured with autologous tumor cells. FIGS. 6A, 6C and 6E are ELISA of supernatants from co-cultures (20:1 effector:target ratio) of autologous tumor cells and PBMCs stimulated with CTA-pulsed or unmodified DCs were analyzed for the levels of the indicated cytokines. All measurement were run in triplicate. Results are displayed as the mean ODs measured with activated PBMCs divided by the mean ODs obtained with PBMCs incubated with autologous DCs without antigens ($OD_{450}$ ratio). FIGS. 6B, 6D and 6F are ELISPOT analysis of IFN-γ expression by patients' CTLs co-cultured with autologous tumor cells (20:1 effector:target ratio) was evaluated using ELISPOT assay as detailed in the Materials and Methods section. Spot counts were performed with an AID ELISPOT Reader System (Cell Technology, Inc., Columbia, Md.) and normalized per 106 PBMCs. Results represent the means±standard deviations of assays run in triplicate. T cell activation and polarization toward the Th1 effector phenotype was shown by the ELISA based measurement of cytokine expression: after stimulation with CTA-pulsed DCs and co-cultured with tumor cells, the levels of IFN-γ and TNF-α were increased by more than 50 times, whereas IL-4, IL-5, and IL-10 were substantially unchanged (as seen in FIGS. 6A, 6C and 6E). The ELISPOT results for IFN-γ further confirmed the increased high occurrence of IFN-γ-producing cells in PBMCs activated with ropporin-presenting DCs co-cultured with autologous tumor cells (FIGS. 6A, 6C and 6E).

SP17/AKAP4/PTTG1 RNA is selectively expressed by NSCLC cell lines and primary tumors, but not in nontumoral cell lines and tissues.

Gene expression of SP17, AKAP4, and PTTG1, was determined with RT-PCR using RNA from a panel of normal tissues (FIG. 1A), three cell lines (two derived NSCLC and one derived from normal bronchus epithelium, FIG. 1B), and a cohort of 17 patients newly diagnosed with NSCLC (FIG. 1C). As a positive control, the present inventors analyzed CTA expression in the testis (6, 16, 17), while negative controls were obtained using pooled RNA that did not undergo retro-transcription (to exclude possible amplification of contaminating genomic DNA) and in which RT-PCR was performed without template (FIGS. 1A-C). While none of the normal tissues expressed detectable RNA levels for SP17, AKAP-4 and PTTG1, (FIG. 1A), the normal bronchial cell line CRL-2503 demonstrated weak expression of SP17 RNA (FIG. 1B). The NSCLC cell lines CRL-5928 and CRL-5922 demonstrated significant RNA expression of the three CTAs evaluated (FIG. 1B). Moreover, tumors from all 17 NSCLC patients were positive for SP17 while 65% of tumors expressed AKAP4 (11/17), and 59% PTTG1 (10/17) (FIG. 1C).

SP17/AKAP4/PTTG1 are expressed at the protein level by NSCLC cell lines and primary patients' samples, but not by normal bronchus epithelium.

To study the expression of our CTA panel at the protein level, the present inventors performed a flow-cytometry analysis by CTA-specific antibody staining of permeabilized cells. FIG. 2 shows that SP17/AKAP4/PTTG1 are expressed by NSCLC-derived but not by normal bronchus-derived cell lines. Of note, nontumoral CRL-2503 cells were negative for SP17 protein, even though the SP17 gene was weakly expressed (FIGS. 1B and 2). The present inventors then performed a similar analysis on patient-derived NSCLC tumors/tissues which was fully consistent with the RT-PCR data. FIG. 2 shows representative results from 3 patients. The specificity of CTA expression was confirmed by the absence of SP17/AKAP4/PTTG1 positive staining in tissues derived from one of the healthy individuals evaluated (a representative result is displayed in FIG. 2). To further assess the expression of selected CTA in tumoral and normal cells, the present inventors performed immunofluorescence analysis of cytospun NSCLC cell lines, a normal bronchus cell line, and cells derived from primary tumors. FIG. 3 shows cytoplasmic localization of SP17/AKAP4/PTTG1 in tumor cells but none or borderline signal in the normal bronchus cell line CRL-2503, in accordance with results from flow-cytometry.

Circulating CTA-specific autoantibodies are detectable in the sera of NSCLC patients.

To measure a possible humoral response against SP17/AKAP4/PTTG1, the present inventors compared the levels of circulating CTA-specific IgG autoantibodies in sera from NSCLC patients with those from healthy subjects, by indirect ELISA. A subject was considered positive if the ELISA signal was at least 3 standard deviations higher than the median signal found in healthy subjects (20). Consistently with expression data from RT-PCR, flow-cytometry and immunofluorescence, FIGS. 4A-C show that the majority of NSCLC patients displayed CTAspecific circulating autoantibodies.

Generation of CTA-specific CTL from patients' PBMCs.

The present inventors successfully generated CTLs capable of efficiently killing autologous tumor cells from 5 patients (FIGS. 5A-F, left). For this analysis, the present inventors selected the patients that displayed specific CTA expression at the protein level in their tumor cells. The specificity of cytotoxic effect was supported by the high percentage of lysis of autologous tumor cells and NSCLC-derived cell lines (40% to more than 80%), whereas nontumoral cells (DC, DC pulsed with the unrelated HPV-E7 antigen, and the normal bronchus-derived cell line CRL-2503) were lysed in <10% (FIGS. 5A-F, right). HLA class I restriction was shown by lysis inhibition by an antibody directed against monomorphic HLA class I molecules, but not HLA class II molecules (FIGS. 5A-F, right). T cell activation and polarization toward the Th1 effector phenotype was shown by the ELISA based measurement of cytokine expression: after stimulation with CTA-pulsed DCs and cocultured with tumor cells, the levels of IFN-γ and TNF-α were increased by more than 50 times, whereas IL-4, IL-5, and IL-10 were substantially unchanged (FIGS. 6A-F, left). The ELISPOT results for IFN-γ further confirmed the increased high occurrence of IFN-γ-producing cells in PBMCs activated with ropporin-presenting DCs co-cultured with autologous tumor cells (FIGS. 6A-F, right).

Although NSCLC was historically thought to be weakly immunogenic because of the low frequency of tumor-infiltrating T cells (21), studies using murine NSCLC models have shown that is it possible to activate an effective immune response utilizing a DC-based approach (22, 23). In addition, tumor antigen-specific T cell responses have been detected in patients with NSCLC (23), indicating that identifying specific NSCLC-associated antigens and presenting them in an optimal fashion to the immune system may generate tumor-specific effector T cells generally absent or inactive in this disease (24). The potential role of immunotherapy in improving patients' survival and reducing morbidities associated to standard treatments has been demonstrated by a recent meta-analysis of 12 clinical vaccine trials in patients with NSCLC (25). When studying an immunotherapy-based anticancer strategy, the choice of antigens to be targeted by the vaccine is a critical step (5). Ideal targets should be highly immunogenic proteins selectively expressed in cancer cells but not in normal cells (5, 10). CTAs are tumor-associated antigens particularly suitable for tumor immunotherapy due to their highly tumor-restricted expression pattern and their immunogenicity (7, 9).

In this study, the present inventors show the use of three CTA, namely SP17, AKAP4, and PTTG1, in the immunotherapy of NSCLC. The present inventors analyzed for the first time the differential expression of 3 CTAs, namely SP17, AKAP4, PTTG1, in a panel of normal tissues, three NSCLC cell lines, one normal bronchus cell line, primary tumor cells from 17 NSCLC patients, and bronchus epithelial cells from 8 healthy subjects. As expected, none of the nontumoral tissues expressed RNA levels for the selected CTAs, with the exception of the testis (7, 10). NSCLC cell lines expressed SP17/AKAP4/PTTG1 transcripts and proteins, while the normal bronchus epithelium cell line showed weakly SP17 RNA expression only. This is consistent with our previous report showing that SP17 is expressed in ciliated somatic epithelia, including those of the airways (26). Interestingly, independent preclinical studies strongly suggest that SP17-directed immunotherapies do not result in any toxicity related to SP17-expression in ciliated cells (16, 27, 28). All of the lung cancer tissues derived from patients demonstrated SP17 expression at the transcriptional and translational levels, while the majority of specimens also displayed AKAP4 and PTTG1 expression. Results for protein expression were confirmed independently by flow-cytometry and immunofluorescence, with consistent results. Tumors from 16 out of 17 NSCLC subjects showed expression of at least two out of three CTAs studied, suggesting their potential importance in this disease. For a protein to serve as a target for immunotherapy it should be able to elicit a strong and measurable immune response, a characteristic known as immunogenicity. The present inventors found that the majority of NSCLC patients' sera were positive for at least two CTA-specific antibodies, with only patient #5 displaying anti-SP17 but not anti-AKAP4 or anti-PTTG1 IgG. While there was a complete concordance between mRNA and protein expression data in tumor tissues, the humoral anti-tumor response, measured as anti-CTA antibodies in sera, resulted more heterogeneous. For example, three NSCLC patients (#2, 13, 14) were classified as anti-SP17 negative, although their tumors expressed SP17. Interestingly, all of the AKAP4- or PTTG1-positive patients also displayed the corresponding specific autoantibodies in their sera. A recent study by Shan Q. et al. (29) generated a low-density protein microarray containing 72 CTAs and probed it with the serum from NSCLC patients and healthy subjects. These investigators reported the detection of NYESO-1, XAGE-1, ADAM29 and MAGEC1 Abs, in the serum of NSCLC patients. These finding indicates anti-CTA antibodies could be exploited as a diagnostic tool in NSCLC.

To determine if SP17/AKAP4/PTTG1 immunogenicity could generate a CTA/tumor-specific CTL response, the present inventors examined T cell response to CTA-loaded dendritic cells (DCs). The application of DCs is a widely recognized method for the stimulation of tumor antigen-specific T cell responses and the present inventors have previously used this technique in MM, cervical and prostate cancer (6, 15, 30, 31). To study the feasibility of generating CTA-specific CTLs from PBMCs, the present inventors selected 5 patients that tested positive for SP17, AKAP4, or PTTG1 protein expression in tumor cells. As expected, patients' PBMCs stimulated with CTA-presenting DCs displayed significant lytic activity against autologous lung cancer cells and NSCLC-derived cell lines. The observed cytotoxic effect was restricted for HLA class I positive targets, as it was blocked by anti-HLA class I but not by anti-HLA class II antibodies. Antigenic specificity for CTL lytic activity was confirmed by their inability to generate a cytotoxic response against the CTA-negative CRL-2503 cells or following exposure to either non-pulsed DCs or DCs loaded with HPV E7 antigen. Cytokine expression analysis revealed that our DC-based CTL generation protocol induced a strong Th-1 polarization in stimulated PBMCs, as confirmed by increased IFN-γ and TNF-α and decreased IL-4, IL-5, and IL-10 levels (6, 16, 19, 31-33). Since NSCLC patients show an abnormal Th-2-type cytokine pattern (34), which negatively impacts a significant response to immunotherapy (35), it is possible, but not a limitation of the present invention, that CTA-loaded DCs have the ability to stimulate a T-helper Th-1 profile. The activation of effector T lymphocytes was further demonstrated by ELISPOT analysis, which revealed a high frequency of IFN-γ-expressing cells in PBMCs primed with CTA-loaded DCs and exposed to autologous tumor cells. This is finding is relevant, since IFN-γ has been shown to exert significant inhibitory effects in NSCLC growth (37).

The feasibility of generating an active CTA-specific immune response in vitro indicates that expression of CTAs by NSCLC cells could have therapeutic relevance and serve as the basis for designing novel immunotherapeutic strategies against this disease. Moreover, DCs engineered in vitro to effectively present CTAs to effector T cells may overcome the immunosuppression seeing in NSCLC's tumor microenvironment allowing the development of effective vaccination strategies against this disease (38-40). CTA-dependent immunotherapies can be developed for NSCLC to determine whether CTA-specific CTL responses could be generated in vivo and overcome the immune tolerance observed in this disease (41-44). In conclusion, these results demonstrate that the CTAs SP17, AKAP-4, and PTTG1, are selectively expressed in NSCLC and that their expression can be exploited to generate specific CTL-mediated antitumor responses. The fact that the present inventors have previously identified the expression and immunogenicity of SP17, AKAP4, and PTTG1 in multiple myeloma, ovarian and prostate cancer (6, 16, 17, 19, 31, 32), and now in NSCLC, indicates that CTA expressing tumors can be targeted with an CTA-driven vaccination strategy.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Siegel R, Naishadham D, Jemal A. Cancer statistics, 2012. CA Cancer J Clin. 2012; 62:10-29.
2. Chrischilles E A, Pendergast J F, Kahn K L, Wallace R B, Moga D C, Harrington D P, et al. Adverse events among the elderly receiving chemotherapy for advanced non-small-cell lung cancer. J Clin Oncol. 2010; 28:620-7.
3. Gadgeel S M. The optimal chemotherapy for stage III non-small cell lung cancer patients. Curr Oncol Rep. 2011; 13:272-9.
4. Siegel R, Naishadham D, Jemal A. Cancer statistics, 2012. CA: A Cancer Journal for Clinicians. 2012; 62:10-29.
5. Mellman I, Coukos G, Dranoff G. Cancer immunotherapy comes of age. Nature. 2011; 480:480-9.
6. Chiriva-Internati M, Yu Y, Mirandola L, D'Cunha N, Hardwicke F, Cannon M J, et al. Identification of AKAP-4 as a new cancer/testis antigen for detection and immunotherapy of prostate cancer. Prostate. 2012; 72:12-23.
7. Caballero O L, Chen Y T. Cancer/testis (CT) antigens: potential targets for immunotherapy. Cancer Sci. 2009; 100:2014-21.
8. Chiriva-Internati M. Sperm protein 17: clinical relevance of a cancer/testis antigen, from contraception to cancer immunotherapy, and beyond. Int Rev Immunol. 2011; 30:138-49.
9. Mathieu M G, Miles A K, Li G, McArdle S E, Rees R C. Cancer/testis antigens for therapeutic use. J Buon. 2009; 14:597-102.
10. Mirandola L, M J C, Cobos E, Bernardini G, Jenkins M R, Kast W M, et al. Cancer testis antigens: novel biomarkers and targetable proteins for ovarian cancer. Int Rev Immunol. 2011; 30:127-37.
11. Bhan S, Negi S S, Shao C, Glazer C A, Chuang A, Gaykalova D A, et al. BORIS binding to the promoters of cancer testis antigens, MAGEA2, MAGEA3, and MAGEA4, is associated with their transcriptional activation in lung cancer. Clin Cancer Res. 2011; 17:4267-76.

12. Chinnasamy N, Wargo J A, Yu Z, Rao M, Frankel T L, Riley J P, et al. A TCR targeting the HLAA* 0201-restricted epitope of MAGE-A3 recognizes multiple epitopes of the MAGE-A antigen superfamily in several types of cancer. J Immunol. 2011; 186:685-96.
13. Kim S H, Lee S, Lee C H, Lee M K, Kim Y D, Shin D H, et al. Expression of cancer-testis antigens MAGE-A3/6 and NY-ESO-1 in non-small-cell lung carcinomas and their relationship with immune cell infiltration. Lung. 2009; 187:401-11.
14. Rao M, Chinnasamy N, Hong J A, Zhang Y, Zhang M, Xi S, et al. Inhibition of histone lysine methylation enhances cancer-testis antigen expression in lung cancer cells: implications for adoptive immunotherapy of cancer. Cancer Res. 2011; 71:4192-204.
15. Chiriva-Internati M, Mirandola L, Yu Y, Jenkins M R, Gornati R, Bernardini G, et al. Cancer testis antigen, ropporin, is a potential target for multiple myeloma immunotherapy. J Immunother. 2011; 34:490-9.
16. Chiriva-Internati M, Yu Y, Mirandola L, Jenkins M R, Chapman C, Cannon M, et al. Cancer testis antigen vaccination affords long-term protection in a murine model of ovarian cancer. PLoS One. 2010; 5.
17. Chiriva-Internati M, Ferrari R, Prabhakar M, Yu Y, Baggoni L, Moreno J, et al. The pituitary tumor transforming gene 1 (PTTG-1): an immunological target for multiple myeloma. J Transl Med. 2008; 6:15.
18. Paillard C, Halle P, Tchirkov A, Confland C, Veyrat-Masson R, Quainon F, et al. NK cytotoxicity and alloreactivity against neuroblastoma cell lines in vitro: Comparison of Europium fluorometry assay and quantification by RT-PCR. J Immunol Methods. 2012; 380:56-64.
19. Chiriva-Internati M, Wang Z, Salati E, Bumm K, Barlogie B, Lim S H. Sperm protein 17 (Sp17) is a suitable target for immunotherapy of multiple myeloma. Blood. 2002; 100:961-5.
20. Santin A D, Bellone S, Palmieri M, Zanolini A, Ravaggi A, Siegel E R, et al. Human papillomavirus type 16 and 18 E7-pulsed dendritic cell vaccination of stage IB or IIA cervical cancer patients: a phase I escalating-dose trial. J Virol. 2008; 82:1968-79.
21. Kim J, Raz D, Jablons D. Unmet need in lung cancer: can vaccines bridge the gap? Clin Lung Cancer. 2008; 9:56-12.
22. Miller P W, Sharma S, Stolina M, Butterfield L H, Luo J, Lin Y, et al. Intratumoral administration of adenoviral interleukin 7 gene-modified dendritic cells augments specific antitumor immunity and achieves tumor eradication. Hum Gene Ther. 2000; 11:53-65.
23. Yasumoto K, Hanagiri T, Takenoyama M. Lung cancer-associated tumor antigens and the present status of immunotherapy against non-small-cell lung cancer. Gen Thorac Cardiovasc Surg. 2009; 57:449-457.
24. Raez L E, Fein S, Podack E R. Lung cancer immunotherapy. Clin Med Res. 2005; 3:221-8.
25. Wang J, Zou Z H, Xia H L, He J X, Zhong N S, Tao A L. Strengths and weaknesses of immunotherapy for advanced non-small-cell lung cancer: a meta-analysis of 12 randomized controlled trials. PLoS One. 2012; 7:5.
26. Grizzi F, Chiriva-Internati M, Franceschini B, Bumm K, Colombo P, Ciccarelli M, et al. Sperm protein 17 is expressed in human somatic ciliated epithelia. J Histochem Cytochem. 2004; 52:549-54.
27. Song J X, Cao W L, Li F Q, Shi L N, Jia X. Anti-Sp17 monoclonal antibody with antibody-dependent cell-mediated cytotoxicity and complement-dependent cytotoxicity activities against human ovarian cancer cells. Med Oncol. 2011; 24:24.
28. Dadabayev A R, Wang Z, Zhang Y, Zhang J, Robinson W R, Lim S H. Cancer immunotherapy targeting Sp17: when should the laboratory findings be translated to the clinics? Am J Hematol. 2005; 80:6-11.
29. Shan Q, Lou X, Xiao T, Zhang J, Sun H, Gao Y, et al. A cancer/testis antigen microarray to screen autoantibody biomarkers of non-small cell lung cancer. Cancer letters. 2012.
30. Santin A D, Hermonat P L, Ravaggi A, Chiriva-Internati M, Zhan D, Pecorelli S, et al. Induction of human papillomavirus-specific CD4(+) and CD8(+) lymphocytes by E7-pulsed autologous dendritic cells in patients with human papillomavirus type 16- and 18-positive cervical cancer. J Virol. 1999; 73:5402-10.
31. Chiriva-Internati M, Wang Z, Salati E, Wroblewski D, Lim S H. Successful generation of sperm protein 17 (Sp17)-specific cytotoxic T lymphocytes from normal donors: implication for tumour-specific adoptive immunotherapy following allogeneic stem cell transplantation for Sp17-positive multiple myeloma. Scand J Immunol. 2002; 56:429-33.
32. Chiriva-Internati M, Ferrari R, Yu Y, Hamrick C, Gagliano N, Grizzi F, et al. AKAP-4: a novel cancer testis antigen for multiple myeloma: Br J Haematol. 2008 February; 140(4):465-8.
33. Chiriva-Internati M, Liu Y, Weidanz J A, Grizzi F, You H, Zhou W, et al. Testing recombinant adeno-associated virus-gene loading of dendritic cells for generating potent cytotoxic T lymphocytes against a prototype self-antigen, multiple myeloma HM1.24. Blood. 2003; 102:3100-7.
34. Asselin-Paturel C, Echchakir H, Carayol G, Gay F, Opolon P, Grunenwald D, et al. Quantitative analysis of Th1, Th2 and TGF-beta1 cytokine expression in tumor, TIL and PBL of non-small cell lung cancer patients. Int J Cancer. 1998; 77:7-12.
35. Ortegel J W, Staren E D, Faber L P, Warren W H, Braun D P. Modulation of tumor-infiltrating lymphocyte cytolytic activity against human non-small cell lung cancer. Lung Cancer. 2002; 36:17-25.
36. Bremnes R M, Al-Shibli K, Donnem T, Sirera R, Al-Saad S, Andersen S, et al. The role of tumor infiltrating immune cells and chronic inflammation at the tumor site on cancer development, progression, and prognosis: emphasis on non-small cell lung cancer. J Thorac Oncol. 2011; 6:824-33.
37. Chen J, Hou J, Zhang J, An Y, Zhang X, Yue L, et al. Atorvastatin synergizes with
IFN-gamma in treating human non-small cell lung carcinomas via potent inhibition of RhoA activity. Eur J Pharmacol. 2012; 682:161-70.
38. Schneider T, Hoffmann H, Dienemann H, Schnabel P A, Enk A H, Ring S, et al. Non-small cell lung cancer induces an immunosuppressive phenotype of dendritic cells in tumor microenvironment by upregulating B7-H3. J Thorac Oncol. 2011; 6:1162-8.
39. Holt G E, Podack E R, Raez L E. Immunotherapy as a strategy for the treatment of non-small-cell lung cancer. Therapy. 2011; 8:43-54.
40. Dubinett S, Sharma S. Towards effective immunotherapy for lung cancer: simultaneous targeting of tumor-initiating cells and immune pathways in the tumor microenvironment: Immunotherapy. 2009 September; 1(5):721-5.

41. O'Callaghan D S, O'Donnell D, O'Connell F, O'Byrne K J. The role of inflammation in the pathogenesis of non-small cell lung cancer. J Thorac Oncol. 2010; 5:2024-36.
42. Sautes-Fridman C, Dieu-Nosjean M C, Damotte D, Fisson S, Fridman W H. The immune microenvironments of lung and intraocular tumors. Bull Cancer. 2011; 98:58-61.
43. Becker S, Markova B, Wiewrodt R, Hoffarth S, Hahnel P S, Pleiner S, et al. Functional and clinical characterization of the putative tumor suppressor WWOX in non-small cell lung cancer. J Thorac Oncol. 2011; 6:1976-83.
44. Xiang R, Mizutani N, Luo Y, Chiodoni C, Zhou H, Mizutani M, et al. A DNA vaccine targeting surviving combines apoptosis with suppression of angiogenesis in lung tumor eradication. Cancer Res. 2005; 65:553-61. 21

What is claimed is:

1. A composition for the treatment of lung cancer comprising:
   an isolated antigen presenting cell that has been loaded with an SP17 tumor associated antigen, an AKAP-4 antigen, and a PTTG1 antigen, wherein the antigen presenting cells activates cytotoxic T lymphocytes against the SP17 tumor associated antigen, the AKAP-4 antigen, and the PTTG1 antigen are expressed in the antigen presenting cells for presentation by Class I MHC, and the cytotoxic T lymphocytes kill one or more lung cancer cells that present one or more of the antigens.

2. The composition of claim 1, wherein the antigen presenting cell is a dendritic cell.

3. The composition of claim 1, wherein the antigen presenting cell is an autologous dendritic cell.

4. The composition of claim 1, wherein the antigen presenting cell is modified to express a nucleotide sequence that codes for a recombinant SP17 tumor-associated antigen and the SP17 tumor-associated antigen is presented via Class I WIC.

5. The composition of claim 1, wherein the antigen presenting cell is modified to express a nucleotide sequence that codes for a recombinant AKAP-4 antigen and the AKAP-4 antigen is presented via Class I MHC.

6. The composition of claim 1, wherein the antigen presenting cell is modified to express a nucleotide sequence that codes for a recombinant PTTG1 antigen and the PTTG1 antigen is presented via Class I MHC.

7. The composition of claim 1, wherein the cytotoxic T lymphocytes have a Th-1 polarization.

8. The composition of claim 1, wherein the lung cancer is a non-small cell lung carcinoma.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
ggcagttctt accaagaaga t                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
ggaggtaaaa ccagtgtcct c                                            21

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
gcgtactctg atactacaat gatg                                         24

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
ggggttttgg gtaaagtca                                               19

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
ggtttaaacc aggagtgccg c                                            21

<210> SEQ ID NO 6
<211> LENGTH: 23
<212> TYPE: DNA
<213> ORGANISM: Artificial Sequence
<220> FEATURE:
```

```
<223> OTHER INFORMATION: Synthetic primer

<400> SEQUENCE: 6
aattcaacat ccagggtcga cag                                    23

<210> SEQ ID NO 7
<211> LENGTH: 17
<212> TYPE: DNA
<213> ORGANISM: Artificial Sequence
<220> FEATURE:
<223> OTHER INFORMATION: Synthetic primer

<400> SEQUENCE: 7
cgtcttcccc tccatcg                                           17

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
ctcgttaatg tcacgcac                                          18
```